(12) United States Patent
Karim

(10) Patent No.: US 9,254,149 B2
(45) Date of Patent: Feb. 9, 2016

(54) SPINAL FIXATION METHOD AND APPARATUS

(75) Inventor: Syed Aftab Karim, Palo Alto, CA (US)

(73) Assignee: Neurosurj Research and Development, LLC, Grand Blanc, MI (US)

( * ) Notice: Subject to any disclaimer, the term of this patent is extended or adjusted under 35 U.S.C. 154(b) by 657 days.

(21) Appl. No.: 13/406,205

(22) Filed: Feb. 27, 2012

(65) Prior Publication Data

US 2013/0184758 A1 Jul. 18, 2013

Related U.S. Application Data

(60) Provisional application No. 61/587,986, filed on Jan. 18, 2012.

(51) Int. Cl.
| | |
|---|---|
| *A61B 17/56* | (2006.01) |
| *A61B 17/68* | (2006.01) |
| *A61B 17/70* | (2006.01) |
| *A61B 17/86* | (2006.01) |
| *A61B 17/80* | (2006.01) |

(52) U.S. Cl.
CPC ........... *A61B 17/683* (2013.01); *A61B 17/7007* (2013.01); *A61B 17/7014* (2013.01); *A61B 17/8635* (2013.01); *A61B 17/7037* (2013.01); *A61B 17/8033* (2013.01)

(58) Field of Classification Search
CPC ............... A61B 17/70; A61B 17/7001; A61B 17/7049; A61B 17/7044; A61B 17/7059; A61B 17/683
See application file for complete search history.

(56) References Cited

U.S. PATENT DOCUMENTS

| | | |
|---|---|---|
| 3,741,205 A | 6/1973 | Markolf et al. |
| 4,950,270 A | 8/1990 | Bowman et al. |
| 4,961,740 A | 10/1990 | Ray et al. |
| 5,098,434 A | 3/1992 | Serbousek |
| 5,169,400 A | 12/1992 | Muhling et al. |
| 5,180,381 A | 1/1993 | Aust et al. |
| 5,324,290 A | 6/1994 | Zdeblick et al. |
| 5,354,299 A | 10/1994 | Coleman |
| 5,364,399 A | 11/1994 | Lowery et al. |
| 5,443,509 A | 8/1995 | Boucher et al. |
| 5,549,431 A | 8/1996 | Royle |
| 5,549,612 A | 8/1996 | Yapp et al. |
| 5,645,547 A | 7/1997 | Coleman |
| 5,647,710 A | 7/1997 | Cushman |
| 5,755,796 A | 5/1998 | Ibo et al. |
| 5,904,683 A | 5/1999 | Pohndorf et al. |

(Continued)

OTHER PUBLICATIONS

International Searching Authority; International Search Report and Written Opinion of the International Searching Authority issued in PCT/US13/21723; Mar. 29, 2013.

(Continued)

*Primary Examiner* — Mary Hoffman
(74) *Attorney, Agent, or Firm* — Jones Walker LLP

(57) ABSTRACT

A spinal stabilization system having a pedicle screw which includes (i) a shaft with external threads and a head segment on one end of the shaft; (ii) a first drive socket positioned in the head segment; (iii) a second drive socket on a shaft end opposite the first drive socket; and (iv) wherein the shaft end opposite the first drive socket has a lesser diameter than the shaft end at the head segment. The system further includes an intervertebral stabilization structure having an elongated body with rotating ring segments attached to each end of the elongated body.

28 Claims, 10 Drawing Sheets

(56) References Cited

U.S. PATENT DOCUMENTS

| | | |
|---|---|---|
| 5,997,541 A | 12/1999 | Schenk |
| 6,379,354 B1 | 4/2002 | Rogozinski |
| 6,383,186 B1 | 5/2002 | Michelson |
| 6,387,129 B2 | 5/2002 | Rieser et al. |
| 6,517,541 B1 | 2/2003 | Sesic |
| 6,533,790 B1 | 3/2003 | Liu et al. |
| 6,613,051 B1* | 9/2003 | Luk et al. .................. 606/250 |
| 6,936,051 B2 | 8/2005 | Michelson |
| 6,964,664 B2 | 11/2005 | Freid et al. |
| 6,969,390 B2 | 11/2005 | Michelson |
| 7,306,605 B2 | 12/2007 | Ross |
| 7,608,096 B2 | 10/2009 | Foley et al. |
| 7,862,594 B2 | 1/2011 | Abdelgany |
| 7,942,909 B2 | 5/2011 | Hammill, Sr. et al. |
| RE42,932 E | 11/2011 | Martin et al. |
| 2002/0087161 A1* | 7/2002 | Randall et al. .................. 606/73 |
| 2003/0036759 A1 | 2/2003 | Musso |
| 2003/0187443 A1 | 10/2003 | Lauryssen et al. |
| 2003/0191472 A1 | 10/2003 | Michelson |
| 2004/0010254 A1 | 1/2004 | Cook et al. |
| 2005/0049593 A1 | 3/2005 | Duong et al. |
| 2006/0104742 A1 | 5/2006 | Fleming |
| 2009/0118764 A1 | 5/2009 | Vaughan et al. |
| 2010/0094345 A1 | 4/2010 | Saidha et al. |
| 2011/0046682 A1* | 2/2011 | Stephan et al. .................. 606/305 |
| 2011/0071576 A1* | 3/2011 | Hadi .................. 606/301 |
| 2011/0137356 A1* | 6/2011 | Kollmer .................. 606/324 |
| 2011/0295319 A1 | 12/2011 | Duplessis et al. |

OTHER PUBLICATIONS

PCT Application No. US2013/021723; International Preliminary Report on Patentability for Applicant Neurosurj Research & Development, LLC dated Jul. 22, 2014.

* cited by examiner

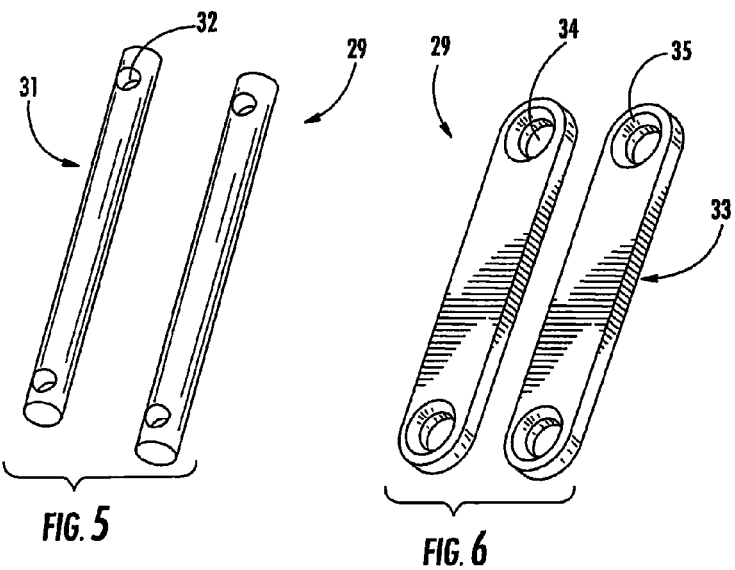
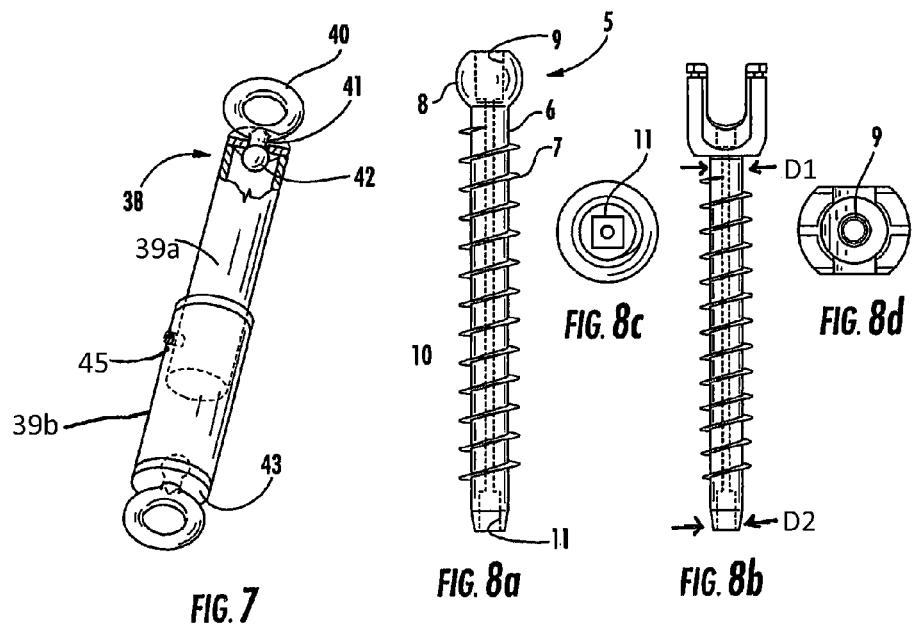

SPINAL FIXATION METHOD AND APPARATUS

This application claims the benefit under 35 USC 119(e) of U.S. provisional application Ser. No. 61/587,986, filed Jan. 18, 2012, which is incorporated by reference herein in its entirety.

FIELD OF INVENTION

The present invention relates to methods and devices for stabilizing the human spine.

BACKGROUND OF INVENTION

Various techniques for spinal stabilization or fusion are known in the art. Such techniques often utilize surgical implants which mechanically immobilize areas of the spine and may include eventual incorporation of grafting material. One technique for spinal fixation includes immobilization of the spine by the use of rods that run generally parallel to the spine. In practicing this technique, the posterior surface of the spine is exposed, and bone screws are first fastened to the pedicles of the appropriate vertebrae or to the sacrum, acting as anchor points for the rods. The bone screws are generally placed two per vertebrae, one at each pedicle on either side of the spinous process. Fasteners join the spine rods to the screws. Some techniques employ anterior fixation devices (i.e., devices position in the anterior side of the vertebrae with screws going into the bodies of the respective vertebrae), in alternative to or in combination with, the posterior devices described above.

BRIEF DESCRIPTION OF THE DRAWINGS

FIG. 5 illustrates one embodiment of an intervertebral stabilization structure.

FIG. 6 illustrates another embodiment of an intervertebral stabilization structure.

FIG. 7 illustrates a further embodiment of an intervertebral stabilization structure.

FIG. 8a illustrates one embodiment of a pedicle screw of the present invention.

FIG. 8b illustrates another embodiment of a pedicle screw of the present invention.

FIG. 8c illustrates a top view of the pedicle screw seen in FIG. 8a.

FIG. 8d illustrates a top view of the pedicle screw seen in FIG. 8b.

DETAILED DESCRIPTION OF SELECTED EMBODIMENTS

Figure 1:
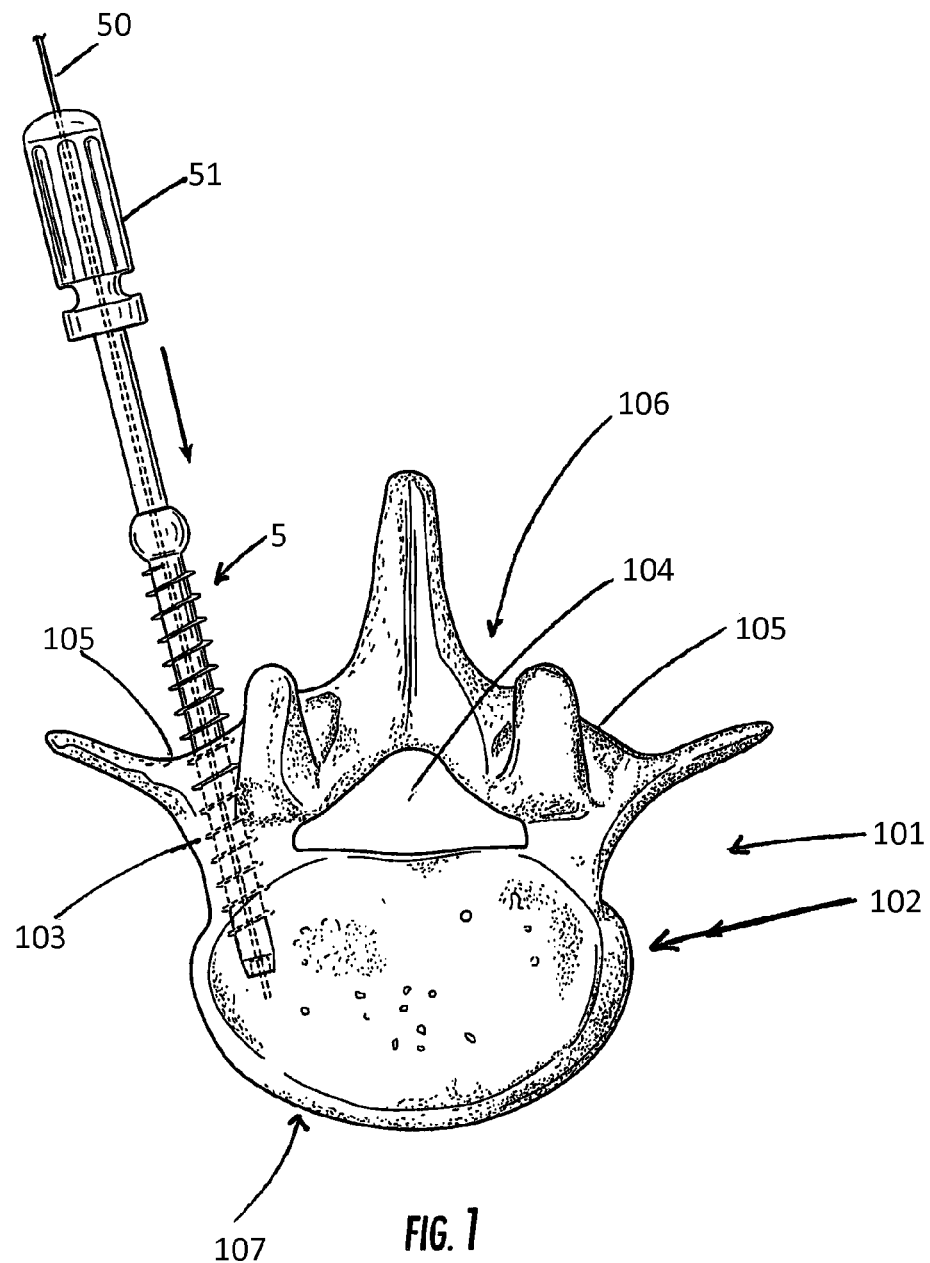
FIG. 1 illustrates an initial step in one method of the present invention.

One embodiment of the present invention is a method for spine stabilization, the steps of which can be generally understood by viewing FIGS. 1-4, 9, and 10. FIG. 1 is a cross-sectional illustration of a vertebra 101. While the figures are of lumbar vertebrae, the methods and structures described herein can be applied to vertebrae in other areas of the spine and the sacrum. FIG. 1 identifies the vertebral body 102, the pedicle 103, the foramen 104, the posterior side or surface 106 of the vertebra (including pedicle entry surface 105), and the anterior side or surface 107 of the vertebra.

In an initial step of the illustrated method embodiment, the patient is placed in the prone position (i.e., with posterior side of the vertebra facing upwards) as suggested by FIG. 1. Thereafter, the posterior pedical entry surface is accessed by a conventional surgical technique, two nonlimiting examples being an open incision technique or a minimally invasive technique such as endoscopic surgery. FIG. 1 suggests where a screw 5 is advanced into the pedicle entry surface 105 of a first vertebra and partially into the vertebral body 102, but without exiting the anterior surface 107 of the vertebral body.

It can be seen that FIG. 1 also illustrates a guide wire 50 extending through the screw 5 and the screw driving tool 51 and into the vertebral body 102. Although not explicitly shown, it will be understood that a conventional technique may be used to place the guide wire into the vertebra prior to attempting to insert the screw 5. In one example, the guide wire has a sharpened tip and is rotated with another tool so the guide wire bores along the path desired for the screw 5 to ultimately follow. An intra-operative imaging technique such as intra-operative x-ray, intra-operative CT, or other specific devices (e.g., an O-Arm® imaging system such as produced by Medtronic, Inc. of Minneapolis, Minn.) may be used to allow the surgeon to advance the guide wire 50 along the desired path. After guide wire 50 is in place, various tools (e.g., drills, screw drivers, and screws) having center passages can be slid along guide wire 50 as suggested in FIG. 1. In the embodiment of FIG. 1, a ratcheting hand drill with a center passage could be employed to form a drill bore along the length of bone tissue into which guide wire 50 extends. Typically guide wire 50 need only extend into the bone far enough to establish the initial trajectory (e.g., 10-15 mm in one example) and the screw is advanced beyond the length of guide wire extending in the bone tissue. As one alternative to drilling with the guide wire itself, the surgeon may use a device such as a "gear shift" to form an initial bore in the bone tissue about 10-15 mm deep along the desired trajectory and insert a guide wire through a central passage in the gear shift and into the bore. The gear shift is then slid off the guide wire while retaining the guide wire in the bore. A screw with a central passage is slid over the guide wire and directed into the bore. A screw driver with a central bore is then used to advance the screw to the desired depth in the bone tissue. Although FIG. 1 and the above examples describe the use of a guide wire 50, the present surgical method may likewise be utilized with other surgical techniques not employing guide wires.

The screw 5 seen in FIG. 1 is illustrated in greater detail in FIGS. 8a to 8d. Screw 5 generally includes the shaft 6 having a series of external threads 7 positioned thereon. The embodiment of FIG. 8a has a spherical head 8 with a first drive socket 9 positioned within the spherical head. While the drive socket 9 in FIGS. 8a and 8d is a polygonal aperture (e.g., square, hexagonal, etc.), the drive socket could take on any shape (e.g., a conventional "straight cut" or "cross-cut" screw driver socket) and could be either a female or male surface for engaging a drive tool and transferring torque from the drive tool to the screw shaft. Screw 5 further includes a second drive socket 11 on the end of shaft 6 opposite the first drive socket 9. Again, second drive socket may be any shape or configuration which allows transfer of torque from a drive tool to the screw shaft. Second drive socket 11 may be the same shape as first drive socket 9 or more be of a different configuration. The embodiment of FIG. 8a includes a central passage or cannulation 10 traveling through shaft 6 from first drive socket 9 to second drive socket 11. However, the invention in not limited to screws with a central passage and alternate embodiment could include screws with a partial passage or a solid shaft, provided the shaft has ends accommodating the first and second drive sockets.

In certain embodiments of the invention, screw 5 will be what is generally known in the surgical art as a "pedicle" screw. For example, these embodiments of screw 5 will have approximate lengths of between about 30 and about 50 mm for more typical situations and lengths as short as 10 mm and as long as 100 mm in less typical situations (although the described embodiments are intended to cover any sub-range of lengths between 10 mm and 120 mm). The diameters of such screws will typically range from about 3.5 to about 6.5 mm or any sub-range of diameters between these dimensions. The smaller size range of screws would be more typical for pediatric patients and the larger size range more typical for large adults. In particular, a screw less than 3.5 mm in diameter could be employed in certain pediatric cases. While the figures illustrate a screw having pedicle-screw-like dimensions, other embodiments may employ screws which may not normally be considered pedicle screws. Nor do such screws need to be threaded along their entire length, but could have threads only along an end section in order to accommodate a mating threaded fastener.

In certain embodiments of screw 5, the shaft end opposite the first drive socket has a lesser outer diameter than the shaft end at the enlarged head segment. For example, in FIG. 8b, the shaft end at second drive head 11 has a diameter $D_2$ which is approximately 80% of the diameter $D_1$ of the shaft end engaging head segment 8, but may alternatively be 70%, 60%, 50% or possibly less of the diameter of the shaft end at the head segment.

Figure 8E:
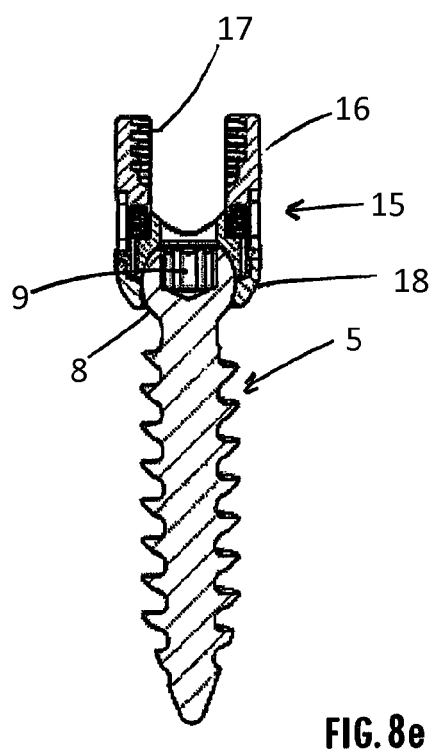
FIG. 8e illustrates a polyaxial connector assembly.
Figure 8F:
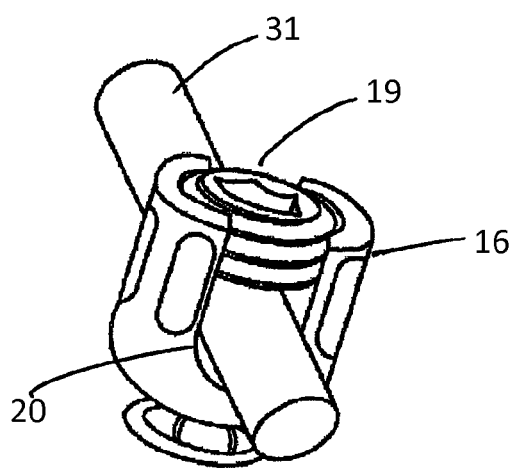
FIG. 8f illustrates a cap screw securing a rod to the polyaxial connector assembly.

One particular embodiment of screw 5 is suggested in FIGS. 8b, 8e, and 8f. As best seen in FIG. 8e, this screw 5 will include the polyaxial connector assembly 15. Polyaxial connector assembly 15 will normally include a upper cup section 15 having opposing U-shaped crenellations 20 and internal threads 17. A lower cup connector 18 will grip the spherical head 8 allowing polyaxial connector assembly to rotate in all directions. As suggested by FIG. 8f, a cap screw 19 will engage internal threads 17 in order to securely grip a rod 31 or other stabilization device within the crenellations 20. Polyaxial connector assemblies are well known in the art, for example see U.S. Pat. No. 7,942,909 which is incorporated by reference herein in its entirety.

As described above, FIG. 1 suggests the screw 5 is advanced into the pedical entry surface of a first vertebra and partially into the vertebral body 102, but without exiting the anterior surface 107 of the vertebral body. One reason for not advancing screw 5 beyond the anterior surface 107 is to avoid the danger of damaging blood vessels positioned adjacent to anterior surface 107; for example, the iliac artery or aorta resting adjacent to the anterior surface of the L3-L5 vertebrae.

Figure 2:
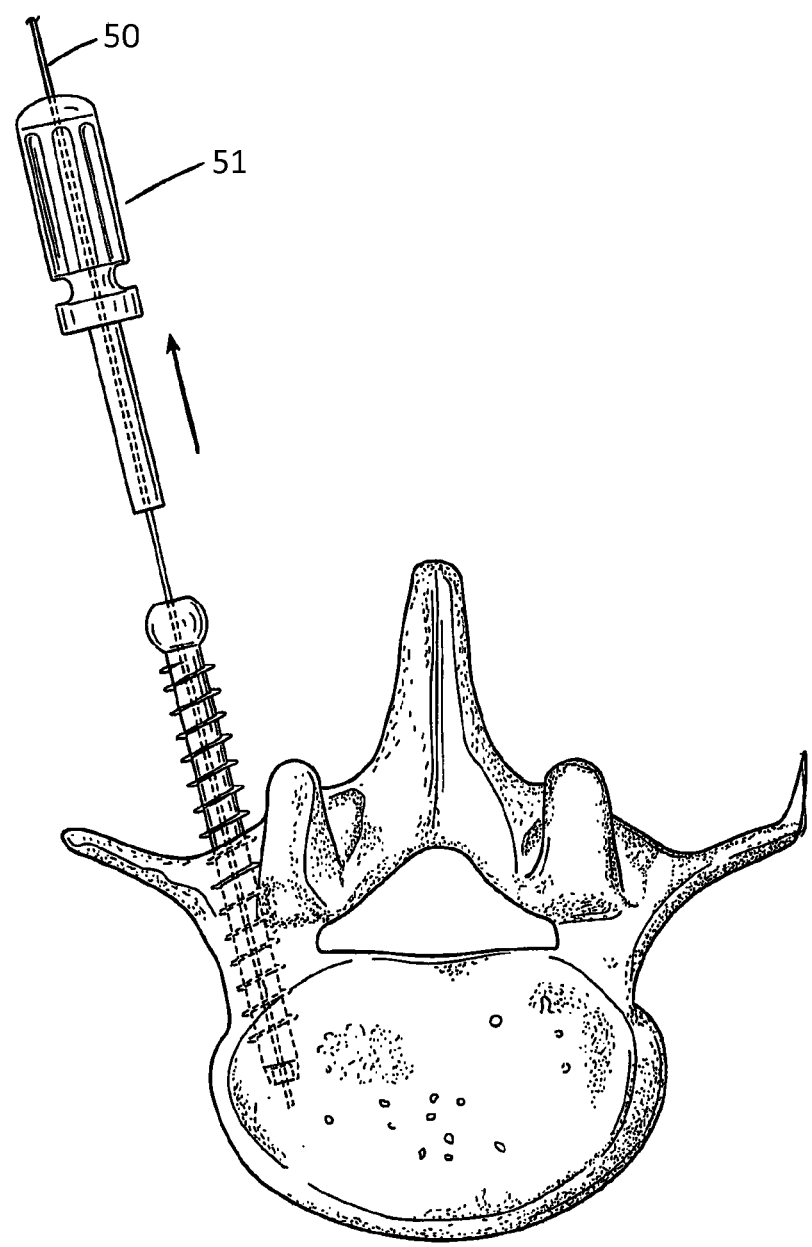
FIG. 2 illustrates a step subsequent to that shown in FIG. 1.
Figure 3:
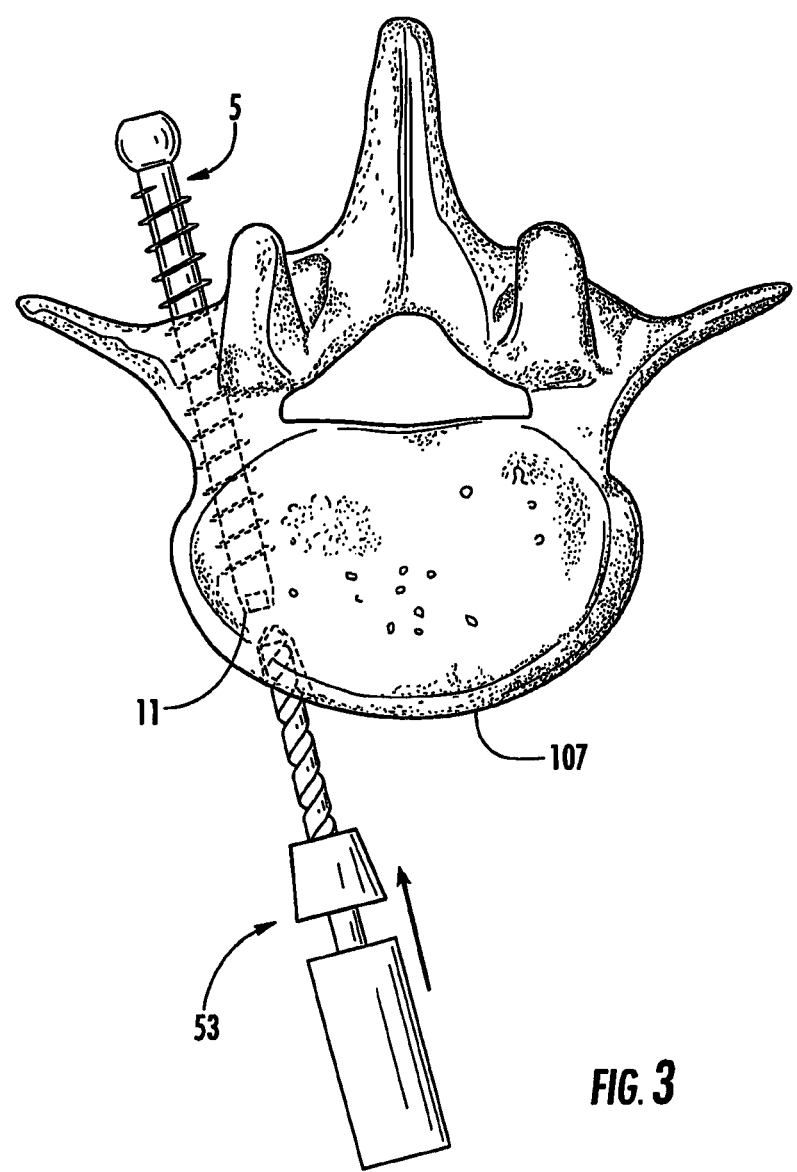
FIG. 3 illustrates a step subsequent to that shown in FIG. 2.
Figure 4:
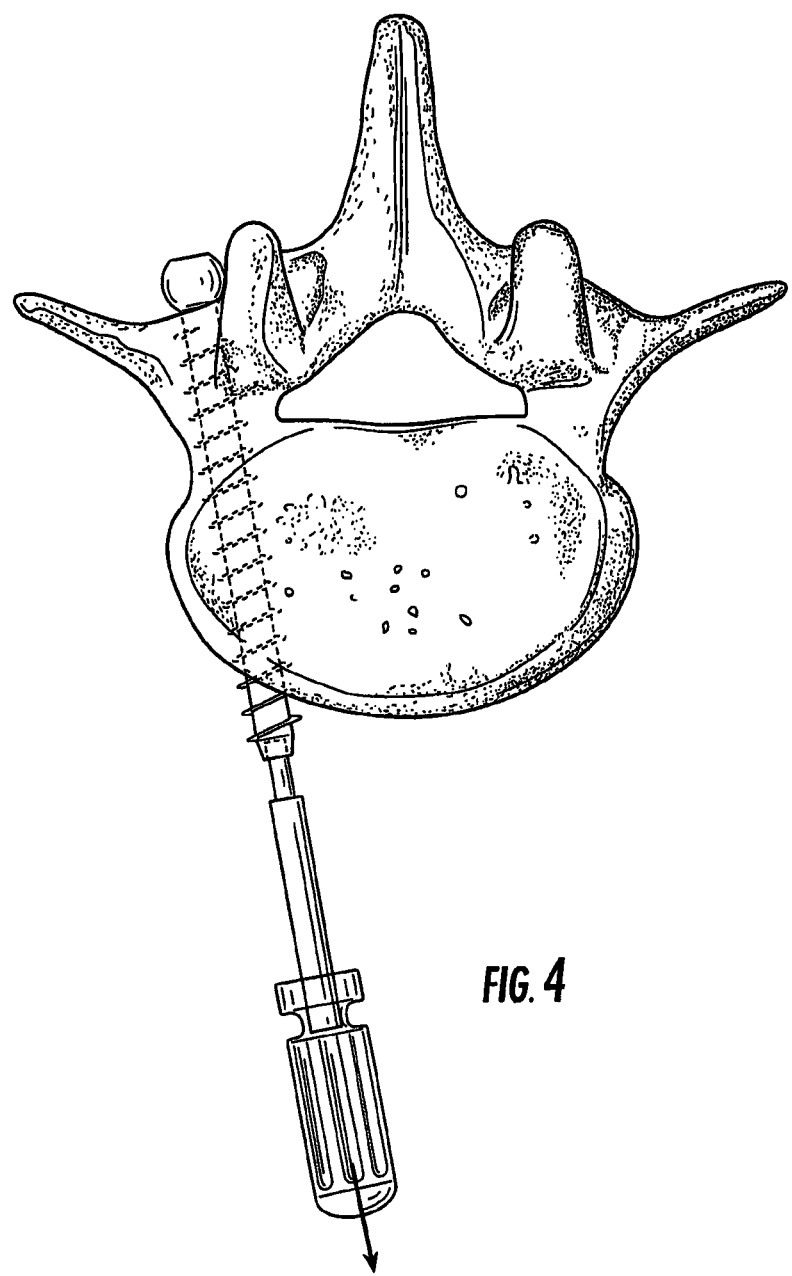
FIG. 4 illustrates a step subsequent to that shown in FIG. 3.

Next, FIG. 2 suggests how the drive tool 51 and guide wire 50 are removed, leaving screw 5 inside of vertebral body 102 but not exiting anterior surface 107. Thereafter, in one preferred embodiment of the method, the patient is then rotated to the supine position. The anterior surface 107 of the vertebral body 102 is then access through open incision technique or a minimally invasive technique as described above. After repositioning any vessels adjacent to the anterior surface section of interest, FIG. 3 suggests how the drill 53 will be used to drill through the anterior surface 107 and into the vertebral body 102 along an axis which will intersect the second drive socket 11 on screw 5. Many different techniques may be used to guide the direction of the drill into the anterior surface 107; for example, a neuronavigation system such as the Medtronic Stealth or Stryker system, AP and lateral x-rays using the O-arm system described above, or the surgeon using his or her judgment to drill pilot holes where the tip of the screw is expected to be encountered. Once the drill has exposed the second drive socket 11, FIG. 4 suggests how drive tool 51 will be used to engage second drive socket 11 and advance screw 5 forward such that its end extends out of the anterior surface 107.

Although not explicitly shown in FIGS. 1-4, it will be understood that the same process for positioning screw 5 through the pedicle and anterior surface 107 will generally be performed bilaterally (i.e., on both the left and right sides of the vertebra) and at two or more levels (i.e., different vertebrae along the spine).

As described in more detail below, FIGS. 9 and 10 suggest how intervertebral stabilization structures (ISS) 27 will be connected to the screws 5 in order to complete the spinal stabilization procedure. The type of ISS 27 employed could vary widely depending on the procedure and FIGS. 5 to 7 are merely three illustrative examples of alternative ISSs. FIG. 5 shows solid cylindrical rods 31 having connecting apertures 32. FIG. 6 illustrates elongated plates 33 having connecting apertures 34 with beveled surfaces 35 allowing a screw head to seat more uniformly and form a lower overall profile. FIG. 7 represents a third type of ISS comprising an elongated body 38 with rotating ring segments 40 attached to each end of the body. In this embodiment, the elongated body 38 is formed by two hollow cylinders 39a and 39b. Cylinder 39b is of a larger diameter and cylinder 39a is of a smaller diameter capable of sliding within cylinder 39b in a telescoping manner. A set screw 45 may be used to fix the relative positions of cylinders 39a and 39b, thereby allowing the length of this ISS to be adjusted to meet the requirements of the individual patient. A rotating ring segment 40 is shown as attached to a shaft 41 which is retained in hollow cylinder 39 by the enlarged end section 42 being larger than the aperture in end cap 43 through which shaft 41 extends. This arrangement allows the ring segment 40 to rotate in order to accommodate variations in screw trajectory and vertebra shape. However, elongated body 38 is not limited to the configuration seen in FIG. 7 and in other embodiments, elongated body 38 need not be telescoping, hollow, or cylindrical. In another embodiment not explicitly shown, shaft 41 could be threaded and engage threads formed in end cap 43, thereby allowing the distance between the two ring segments 40 to be adjusted in a manner similar to a conventional "turnbuckle" device. Structures such as seen in FIG. 7 may be referred to as "polyaxial stabilization structures" in the sense that they allow a rotative connection to the screws 5. Nor is the particular ISS in anyway limited to those shown in the figures, but could include virtually any existing of future developed ISS.

Figure 9:
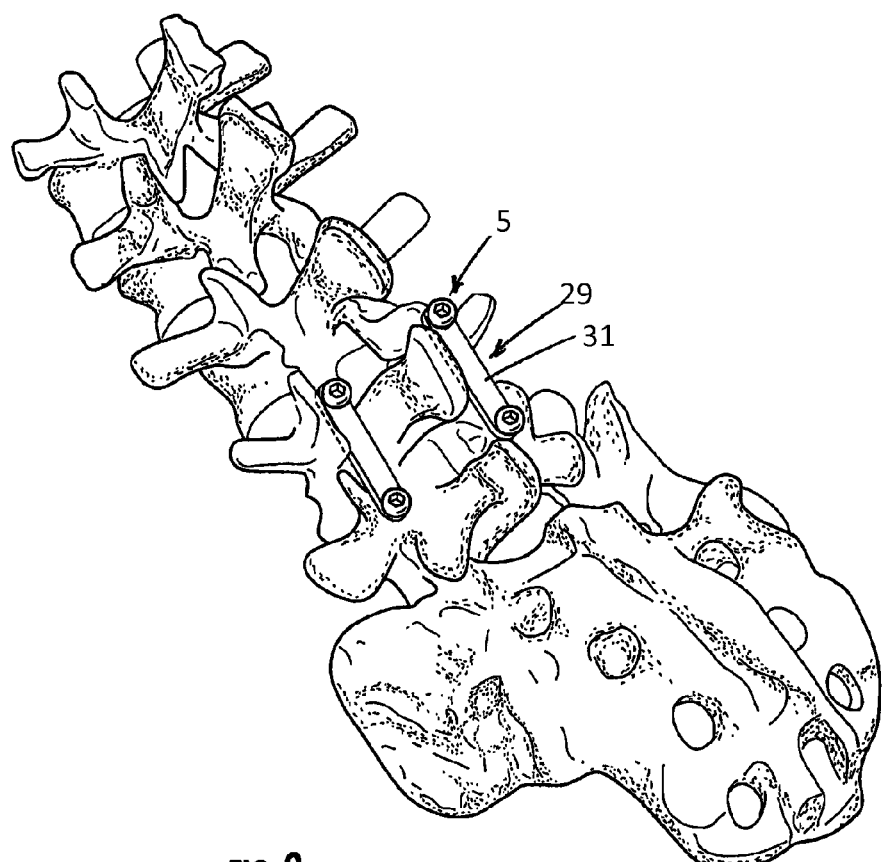
FIG. 9 illustrates one embodiment of intervertebral stabilization structures positioned along the posterior surface of the spine.
Figure 10:
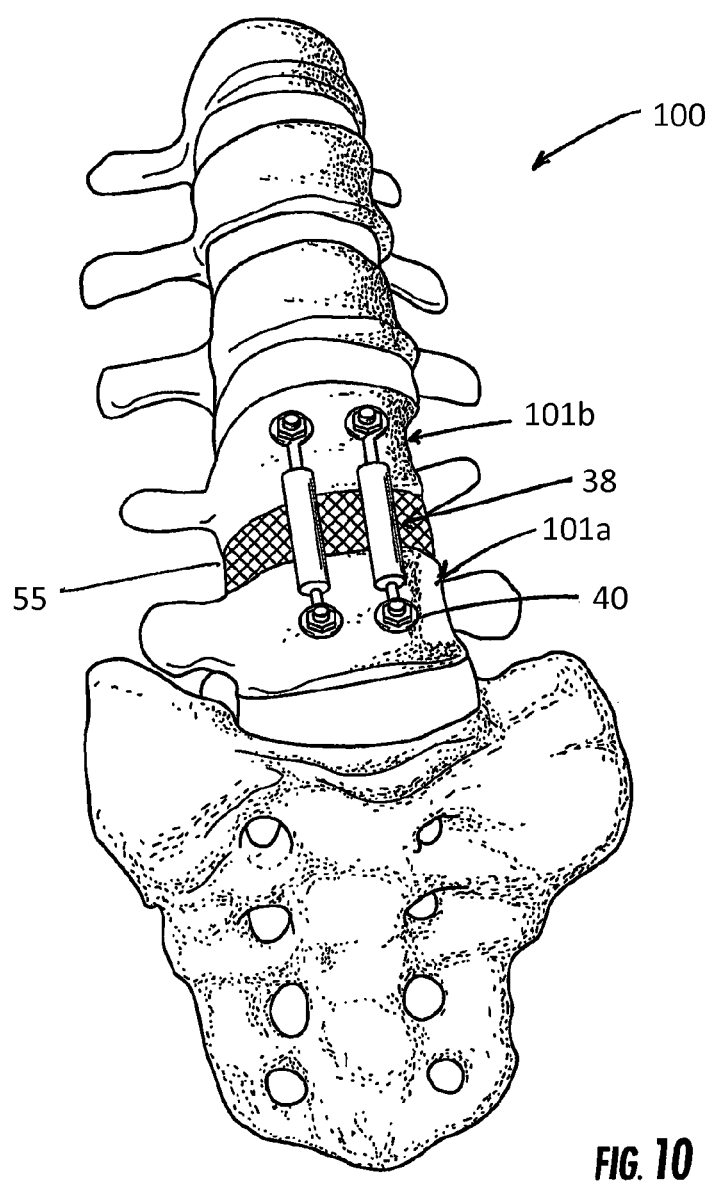
FIG. 10 illustrates another embodiment of intervertebral stabilization structures positioned along the anterior surface of the spine.

Viewing FIG. 9, this nonlimiting example suggest how the ISSs 29 on the posterior side of the spine are rods 31 which have the screws 5 extending through the rod aperture 32. FIG. 9 illustrates two ISSs 29 arranged in an ipsilateral manner (i.e., one ISS on each side of the posterior surface of the spine). Although FIG. 9 shows the ISSs 29 connected to adjacent vertebrae, it will be understood that the ISSs could also be connected to nonadjacent vertebrae (i.e., the connection skipping one or more vertebrae). Naturally this is merely one manner of connecting the ISSs to the screws and any number of connections mechanism could be employed, e.g., a polyaxial connector assembly with the rods 31 held in crenellations 20 by cap screws 19 as seen in FIG. 8*f*. Viewing the anterior side of the spine as shown in FIG. 10, this variation employs the ISSs having the ring segments 40 and shows the ends of screws 5 extending through ring segments 40 to the extent need to fix threaded nut-fasteners on the ends of screws 5. While FIGS. 9 and 10 show the ISSs fixed to adjacent vertebrae, other method embodiments could skip one or more levels between vertebrae to which the ISSs are attached, or have the ISSs attached to three or more vertebrae.

Figure 11:
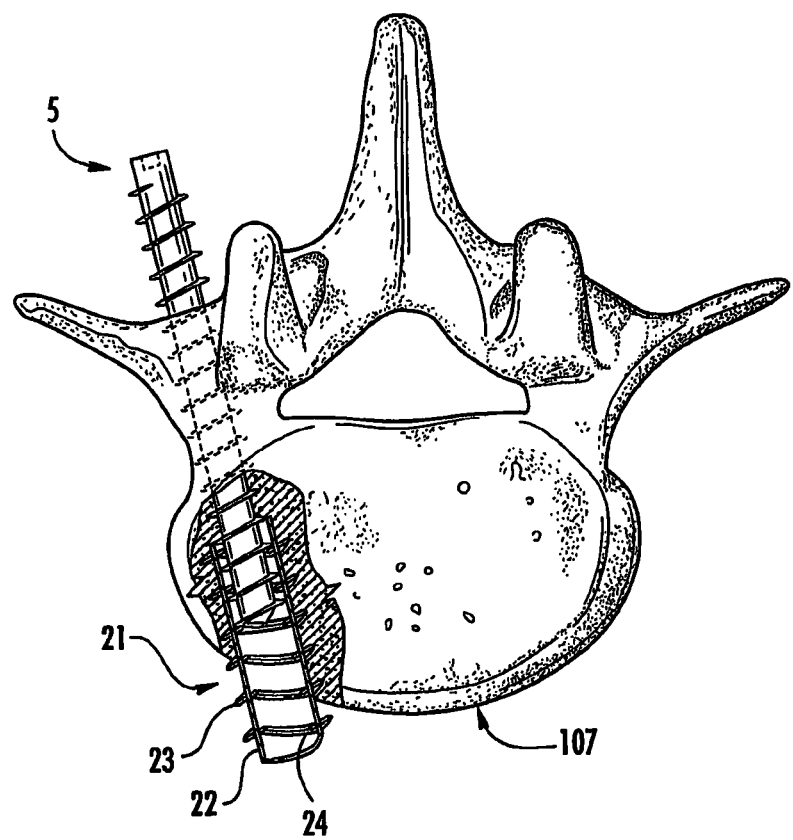
FIG. 11 illustrates another embodiment of hardware for securing the pedicle screw in the vertebral body.

A further embodiment shown in FIG. 11 suggests another fastener device to engage screw 5. In this embodiment, the cylindrical fastener 21 includes a hollow cylindrical body 22 having both external threads 23 and internal threads 24. A bore would be drilled into anterior vertebra surface 107 to accommodate cylindrical body 22. As suggested in the cutaway portion of FIG. 11 showing the living bone tissue, the external threads 23 would grip the bone tissue to secure fastener 21 within the vertebral body. Although not seen in FIG. 11, the end of cylindrical body 22 extending from the vertebral body could include any type of surface allowing a tool to apply torque to cylindrical body 22. Screw 5 advancing through the pedicle and into the vertebral body would then be able to engage the internal threads 24 to be secured in place. Preferably, cylindrical fastener 21 will be positioned such that screw 5 may advance a good distance into vertebral body 107 before engaging cylindrical fastener 21. An ISS could be attached to fastener 21 in any convention manner. For example, another screw (not illustrated) could pass through the ISS and engage the internal threads 24 of fastener 21.

There are many surgical procedures where the above described method may be employed. Nonlimiting examples could include: anterior or posterior fusions (particularly lumbar fusions) using a pair of ISSs on the anterior or posterior sides of the spine; these could include anterior lumbar interbody fusion (ALIF) procedures where stabilization structures are positioned only on the anterior side of the spine; or "360.degree." ALIF procedures where two parallel ISSs are positioned on the anterior side and two parallel ISSs are positioned on the posterior side of the spine. Other example procedures include stabilizations of lumbar burst fractures or lumbar corpectomies using anterior and posterior ISSs to create 360.degree. stabilization system as suggested in FIGS. 9 and 10; for example a an L4 corpectomy (i.e., connecting the L3 to the L5 vertebra) or an L5 corpectomy (i.e., connecting the L4 to the S1 vertebra). FIG. 10 also illustrates the positioning of a interbody graft 55 between vertebral bodies 101*a* and 101*b* which could be employed in many stabilization techniques.

Although the method embodiments described above contemplated turning the patient from the prone position to the supine position, other embodiments could potentially perform the posterior and anterior access to the spine while the patient in the lateral position (i.e., on the patient's side), thereby eliminating the need to turn the patient during the procedure. Nor do all method steps need to be practiced in the order discussed above, but in particular situations, the steps could be carried out in a different order.

Figure 12:
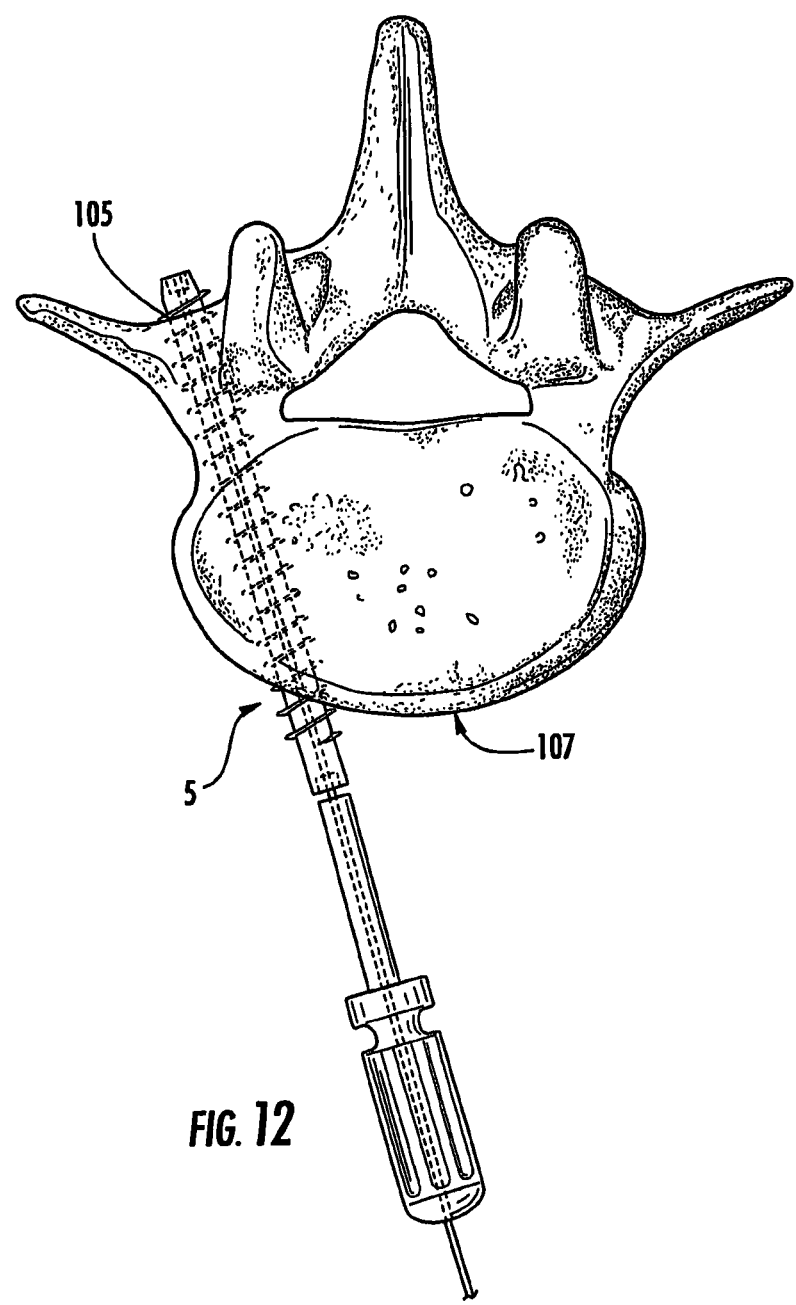
FIG. 12 illustrates an alternative method with the pedicle screw being advanced through the vertebral body from the anterior side to the posterior side.

A still further variation in the invention is seen in FIG. 12. FIG. 12 illustrates an alternative method where the screw 5 is inserted from the anterior side into the vertebral body and is advanced along a trajectory which has the screw exiting out of the posterior pedicle surface 105. This embodiment of screw 5 is slightly different in that it lacks a spherical head in order to accept a lower profile ISS and securing nut-type fastener (as opposed to a spherical head used with polyaxial connector devices). In this embodiment, each end of the screw may project 10-30 mm (and more preferably 10-20 mm) outside the bone tissue, which suggests the screw should have a length of between 50 and 120 mm, and more preferably between 70 and 100 mm. The trajectory of the screw could be obtained using any of the surgical navigation techniques described above. The method of FIG. 12 has the advantage of allowing the distal end of screw 5 to actually exit posterior pedicle surface 105 (thereby eliminating the danger of striking blood vessels) and eliminating the step of drilling into bone tissue to locate the tip of screw 5.

While the above embodiments have been described in terms of methods of spinal stabilization, the present invention also includes the various apparatuses described in carrying out the methods. For example, a further embodiment of the invention includes a pedicle screw having a cannulated shaft with external threads and an enlarged head segment on one end of the shaft. A first drive socket is positioned in the enlarged head segment and a second drive socket on a shaft end opposite the first drive socket. Another embodiment includes a spinal stabilization system which include a pedicle screw and an intervertebral stabilization structure. The pedicle screw has a shaft with external threads and a head segment on one end of the shaft, a first drive socket positioned in the head segment, and a second drive socket on a shaft end opposite the first drive socket. The intervertebral stabilization structure has an elongated body with rotating ring segments attached to each end of the elongated body.

Another alternative method for spine stabilization comprises the steps of: (a) accessing the anterior side of the spine, (b) advancing a screw into the anterior side of the spine and toward the posterior pedicle surface of a first vertebra until the screw exits the posterior pedicle surface, (c) repeating steps (a) and (b) at a second vertebra, (d) wherein the screw comprises: i) a first drive socket; (ii) a threaded shaft extending from the first drive socket; (iii) a second drive socket on a shaft end opposite the first drive socket, and (iv) a length such that 10-30 mm of the screw extends from both the pedicle surface and the anterior surface; and (e) wherein intervertebral stabilization structures are fixed between the first and second vertebra by attaching to the screws on the posterior side of the spine and the anterior side of the spine.

A still further embodiment is a spinal stabilization system comprising: (a) a pedicle screw comprising: (i) a shaft body with external threads and first and second shaft ends; (ii) a first drive socket positioned on the first shaft end; (iii) a second drive socket on the second shaft end; (iv) wherein the shaft has a length of between about 60 mm and about 120 mm; and (b) an intervertebral stabilization structure comprising an elongated body with an aperture for sliding over either the first or second shaft end. Alternatively in this embodiment, the shaft end opposite the first drive socket may a lesser diameter than the shaft end at the head segment. While the invention has been described in terms of certain specific embodiments, those skilled in the art will understand that there are many obvious variations and modifications of the described embodiments. All such variations and modifications are intended to come within the scope of the following claims.

The invention claimed is:

1. A method for spine stabilization comprising the steps of:
   a) accessing the posterior side of a subject's spine, advancing a screw into the pedical entry surface of a first vertebra and partially into the vertebral body, but without exiting the anterior side of the vertebral body,
   b) repeating step (a) at a second vertebra;
   c) wherein the screws each comprise:
      i) a first drive socket;
      ii) a threaded shaft extending from the first drive socket; and
      iii) a second drive socket on a shaft end opposite the first drive socket;
   d) accessing the anterior side of the spine, in both the first and second vertebra, drilling through an anterior surface of the vertebral body until the second drive sockets of the screws are encountered;
   e) engaging the second drive sockets and advancing the screws toward the anterior surface of the vertebral body;
   f) wherein at least one intervertebral stabilization structure is fixed between the first and second vertebra by attaching to the screws on at least one of the posterior side of the spine or the anterior side of the spine.

2. The method of claim 1, where at least one intervertebral stabilization structure is positioned on each of the posterior side of the spine and the anterior side of the spine.

3. The method of claim 1, where the posterior side of the spine is accessed with the subject in the prone position and the anterior side of the spine is accessed with the subject in the supine position.

4. The method of claim 1, where in step (e), the screws are further advanced beyond the anterior surface of the vertebral body.

5. The method of claim 1, where the intervertebral stabilization structure is positioned along the pedical entry surface to an end of the screw having the first drive socket.

6. The method of claim 1, where the intervertebral stabilization structure is positioned along the anterior surface and connected to an end of the screw having the second drive socket.

7. The method of claim 1, further comprising two stabilization structures positioned in an ipsilateral manner.

8. The method of claim 1, further comprising two stabilization structures where the stabilization structures are connected to either (1) adjacent vertebrae; or (2) nonadjacent vertebrae.

9. The method of claim 1, where the anterior surface of the first and second vertebral body is accessed in either an open incision technique or a minimally invasive technique.

10. The method of claim 1, where the stabilization structure is at least one of rods, elongated plates, or a polyaxial stabilization structure.

11. The method of claim 1, where a polyaxial connector assembly is attached to the screws on at least one of a posterior or anterior side.

12. The method of claim 1, where a central passage extends through the screw shaft and drive sockets.

13. The method of claim 1, where the screw is cannulated and a guide wire is positioned into the pedicle prior to advancing the screw along a path established by the guide wire.

14. The method of claim 1, where the first drive socket is a polygonal aperture formed in an enlarged head section of the screw and the second drive socket is a polygonal aperture in the opposite shaft end.

15. The method of claim 1, where the first and second vertebrae are in the lumbar region.

16. The method of claim 1, where the first and second vertebrae are adjacent vertebrae.

17. The method of claim 1, where the intervertebral stabilization structure comprises an elongated body with rotating ring segments attached to each end of the elongated body.

18. The method of claim 17, where the ring segments have a shaft with an enlarged section retained in the elongated body.

19. The method of claim 17, where the elongated body is cylindrical in shape.

20. The method of claim 1, where the screw includes a polyaxial connector assembly attached to an end of the screw having the first drive socket.

21. The method of claim 20, where the intervertebral stabilization structure is attached to the polyaxial assembly with a cap screw.

22. The method of claim 1, where a hollow cylindrical fastener having external and internal threads is advanced into the anterior surface in line with the screw.

23. The method of claim 22, where the screw engages the internal threads of the hollow cylindrical fastener.

24. The method of claim 23, where the screw advancing into the vertebral body engages the internal threads of the hollow cylindrical fastener.

25. The method of claim 1, further comprising the step of performing a partial or complete corpectomy procedure.

26. The method of claim 7, where the method is performed as part of a lumbar interbody fusion.

27. The method of claim 1, where the posterior side of the spine and/or the anterior side of the spine are accessed with the subject in the lateral decubitus position.

28. The method of claim 15, where the method is being perform to treat a fracture of the L5 vertebra.

* * * * *